United States Patent [19]

Selmer et al.

[11] Patent Number: 5,387,503
[45] Date of Patent: Feb. 7, 1995

US005387503A

[54] ASSAY METHOD USING INTERNAL CALIBRATION TO MEASURE THE AMOUNT OF ANALYTE IN A SAMPLE

[75] Inventors: Johan Selmer, Farum; Fritz Poulsen, Hillerød, both of Denmark

[73] Assignee: Novo Nordisk A/S, Bagsvaerd

[21] Appl. No.: 938,039

[22] PCT Filed: Jun. 6, 1991

[86] PCT No.: PCT/DK91/00151

§ 371 Date: Nov. 12, 1992

§ 102(e) Date: Nov. 12, 1992

[87] PCT Pub. No.: WO91/19196

PCT Pub. Date: Dec. 12, 1991

[30] Foreign Application Priority Data

Jun. 6, 1990 [DK] Denmark ............................. 1380/90

[51] Int. Cl.$^6$ ................. G01N 33/543; G01N 33/566; G01N 33/569
[52] U.S. Cl. .......................................... 435/5; 435/7.2; 435/7.21; 435/7.23; 435/7.32; 435/7.4; 435/7.8; 435/7.94; 435/7.95; 435/967; 435/975; 436/501; 436/518; 436/807
[58] Field of Search ................... 435/5, 7.2, 7.21, 7.23, 435/7.32, 7.4, 7.8, 7.94, 7.95, 967, 975; 436/501, 518, 807

[56] References Cited

U.S. PATENT DOCUMENTS

| | | | |
|---|---|---|---|
| 4,533,629 | 8/1985 | Litman et al. | 435/188 |
| 4,540,659 | 9/1985 | Litman et al. | 435/188 |
| 4,791,056 | 12/1988 | Sizto et al. | 435/188 |
| 4,849,338 | 7/1989 | Litman et al. | 435/436 |

FOREIGN PATENT DOCUMENTS

| | | |
|---|---|---|
| 77274/91 | 9/1991 | Australia . |
| 0253464 | 3/1986 | European Pat. Off. . |
| 0249418 | 12/1987 | European Pat. Off. . |
| 0269352 | 6/1988 | European Pat. Off. . |
| 0343932 | 11/1989 | European Pat. Off. . |
| 2187283 | 9/1987 | United Kingdom . |

OTHER PUBLICATIONS

Oellerich et al., Scand. J. of Clin. & Lab. Invest. Supp. 193, vol. 49, pp. 62–71 (1989).
Litman et al., Clin. Chem., vol. 29, No. 9, pp. 1598–1603 (1983).
Anderson et al., Clin. Chem., vol. 32, No. 9, pp. 1692–1695 (1986).

*Primary Examiner*—David Saunders
*Attorney, Agent, or Firm*—Steve T. Zelson; Elias J. Lambiris

[57] ABSTRACT

This invention relates to a method of determining the amount of test analyte in a sample using internal calibration comprising mixing a sample with a predetermined amount of a calibrator analyte foreign to the sample and with a comparable behavior in an assay to that of the test analyte, contacting the mixture with a solid support containing, each in a separate area, a regent for binding the test and calibrator analytes, respectively, contacting the solid support with a mixture of labelled reagents for binding the test and calibrator analytes, respectively, and determining the amount of test analyte in the sample by comparing the levels of labelled reagent bound to the test and calibrator analytes.

55 Claims, No Drawings

ASSAY METHOD USING INTERNAL CALIBRATION TO MEASURE THE AMOUNT OF ANALYTE IN A SAMPLE

FIELD OF INVENTION

The present invention relates to a method for determining the amount of a test analyte in a sample using internal calibration, as well as to a test kit for use in the method.

BACKGROUND OF THE INVENTION

Quantitative assays involving the binding of a given test analyte in a sample to a reagent present on a solid support make use of calibrators with which the samples tested in the assays are compared. In some assay systems, such as the radio-immunoassay (RIA) or enzyme-labelled immunosorbent assay (ELISA), where analyses of many samples are conducted simultaneously, it is ususal and convenient to include appropriate calibrators. However, when analyses are made of one sample at a time, which is typical of "doctor's office" assays, the inclusion of a set of calibrators for each sample will make the test more difficult and expensive to carry out. The results from the assays of such samples are therefore most often compared to the results obtained with a set of previously generated calibrators which is used over and over again.

Such externally calibrated assays cannot take account of variations in assay parameters such as incubation time, the temperature at which the assay is conducted, the liquid volumes of the sample and reagents and the concentration of reagents.

In an attempt to remedy the drawbacks inherent in using external calibration in an assay, EP 253 464 discloses a method of providing internal calibration in an assay in which a receptor for an analyte in a sample and a receptor for a conjugate of an analyte receptor with a label substance are immobilized in two separate areas on a solid support. The solid support is contacted with a sample containing the analyte to bind any analyte in the sample to the analyte receptor, after which the solid support is contacted with the conjugate which binds to the analyte in the sample as well as to the receptor for the conjugate.

Although the internal calibration provided in this assay takes several of the possible variations influencing signal development into account, the assay still has to be performed carefully with respect to the volume of the sample added, which means that the system remains relatively sensitive to outside influence. Thus, if a double volume of the sample is erroneously added, the concentration of analyte determined for the sample will be the double of the actual concentration.

The object of the present invention is to provide an assay method based on internal calibration for determining the concentration of a test analyte in a sample, which method does not show variations with respect to the above-mentioned critical parameter.

SUMMARY OF THE INVENTION

The present invention is based on the observation that assays for different analytes may be adjusted to progress in substantially the same manner, resulting in calibration curves for different assays which are comparable in that they tend to be parallel. This means that a calibration curve for one analyte assay may be used to calibrate another analyte assay provided that the conversion factor between the two calibration curves obtained in the two assays is known.

Accordingly, the present invention relates to a method of determining the amount of a test analyte in a sample, the method comprising
 (a) mixing a sample of a known volume with a predetermined amount of a calibrator analyte which is foreign to the sample in question, and which is so selected that its behaviour in an assay is comparable to that of the test analyte under the same assay conditions,
 (b) contacting the mixture prepared in step (a) with a solid support to which is bound, in a first discrete area, a reagent capable of selectively binding the test analyte and, in a second discrete area, a reagent capable of selectively binding the calibrator analyte,
 (c) subsequently contacting the solid support with a mixture of a labelled reagent capable of selectively binding the test analyte and a similarly labelled reagent capable of selectively binding the calibrator analyte, and
 (d) determining the amount of test analyte in the sample by comparing the levels of labelled reagent bound to the test and calibrator analytes, respectively.

In another aspect, the present invention relates to a test kit for determining the amount of a test analyte in a sample, comprising, in separate containers,
 (a) a predetermined amount of a calibrator analyte which is foreign to the sample in question,
 (b) a solid support to which is bound, in a first discrete area, a reagent capable of selectively binding the test analyte and, in a second discrete area, a reagent capable of selectively binding the calibrator analyte,
 (c) a labelled reagent capable of selectively binding the test analyte, and
 (d) a similarly labelled reagent capable of selectively binding the calibrator analyte,
the labelled reagents (c) and (d) being optionally provided as a mixture thereof in a single container.

In the present context, the term "test analyte" is intended to indicate a substance the concentration of which in the sample is to be measured; the test analyte is a substance for which a specific receptor exists. The term "calibrator analyte" is intended to indicate a substance used to calibrate the test analyte assay; it is also a substance for which a specific receptor exists (distinct from the receptor for the test analyte). A "receptor" may, for the present purpose, be defined as a substance which is able to recognize and bind to a distinctive structure on an analyte; thus, the reagents used in steps (b) and (c) of the method of the invention may be defined as receptors for the test and calibrator analytes, respectively.

By mixing the predetermined amount of calibrator analyte with the sample rather than adding it in a subsequent step as in the assay described in EP 253 464, identical assay conditions are ensured for the test and calibrator analytes from the outset. The initial mixing permits the use of larger sample volumes which, in turn, makes it easier to adjust the assay system to the correct ratio of calibrator analyte to sample so that no allowances will have to be made for this ratio in subsequent steps of the assay. Thus, when withdrawing a test volume from the mixture of sample and calibrator in step (b) of the present method, it will not have to be accurately measured. As the calibrator analyte is one which is not found naturally in the sample to be analysed, the response obtained in the calibrator analyte assay will be derived from the added amount of calibrator analyte alone, thereby avoiding erroneous results. The term "comparable" is intended to mean that a calculable correspondence exists between the calibration curves of the test analyte and calibrator analyte assays, respectively, produced under similar reaction conditions. The correspondence is obtained by selecting suitable reagents (e.g. antibodies with suitable affinities), varying the composition of the reagents and adjusting their concentration, in a manner known to a person skilled in the art.

When, for carrying out step (c) of the method of the invention, a mixture of the labelled reagents is prepared, this is done to make the measurement of the analyte in the assay independent of variations in step (c), e.g. variations in the relative amounts of labelled reagents, incubation time and temperature. The label substance used to label the reagents may be defined as a substance which either in itself or by being reacted with another compound (such as a substrate) is capable of generating a detectable signal.

In the known assay using internal calibration, the calibrating system consists of a calibrator receptor which is able to bind the analyte receptor conjugate (EP 253 464). At larger sample volumes, a larger amount of test analyte will be bound to the analyte receptor. However, since the same amount of conjugate will be bound to the calibrator receptor, this will erroneously appear in the assay as an increased concentration of the analyte.

The assay of the present invention is less sensitive to a variety of parameters such as reaction time, liquid volumes of sample and reagents and temperature so that less accuracy is required to carry out the assay. This makes the assay particularly suitable for doctor's office tests. In particular, it has been found that, unlike the previously known internal calibration assays, the present way of calibrating the assay permits correction for test volume which is a critical factor for obtaining accurate determination results.

DETAILED DESCRIPTION OF THE INVENTION

The method of the invention is suitable for quantitating test analytes of biological origin (i.e. produced by living organisms). Examples of such test analytes are hormones, e.g. insulin, growth hormone, chorionic gonadotropin, luteinising hormone, follicle stimulating hormone, steroid hormones; pancreatic amylase; heart structural proteins; C-reactive protein; α-foetoprotein; creatine kinase type MB or MM: blood components, e.g. blood coagulation factors such as Factor VII, Factor VIII, Factor IX, Factor X or Factor XIII, or proteolytic enzymes or precursors thereof such as thrombin, prothrombin, plasmin, plasminogen or tissue plasminogen activator; growth factors, e.g. insulin-like growth factor, platelet-derived growth factor, epidermal growth factor, colony stimulating factor, transforming growth factor or fibroblast growth factor; microbial components such as bacterial or viral surface proteins or toxins, e.g. cholera toxin, diphtheria toxin, Salmonella toxin, Shiga toxin, *Clostridium botulinum* toxin, aflatoxin, endotoxin or Chlamydia-specific antigen (e.g. LPS); or antibodies (e.g. antibodies raised in the human or animal body against pathogens).

Particularly preferred test analytes to be quantitated according to the method of the invention are creatine kinase type MB or MM, pancreatic amylase, heart structural proteins, C-reactive protein, α-foetoprotein or Chlamydia-specific antigen.

The sample may be any fluid containing a dissolved or dispersed material of biological origin. Thus, the sample may be selected from a body fluid, e.g. blood, serum, plasma, amniotic fluid, sputum, urine, cerebrospinal fluid, lymph, tear fluid, faeces or gastric fluid, a tissue extract, a culture medium in which a cell has been grown or a foodstuff (to test for the presence of contaminants such as pathogens or their toxins therein). If the sample is not in itself sufficiently fluid for the present purpose, it may be admixed with a suitable fluid to the desired fluidity, for instance by homogenization.

The calibrator analyte should be one which is not found naturally in the sample in question, and the calibrator analyte assay should exhibit a calibration curve which is comparable to the calibration curve for the test analyte assay produced under the same reaction conditions. The calibrator analyte should furthermore be stable, in particular storage stable. Examples of suitable calibrator analytes are proteins which do not cross-react with the test analyte, e.g. animal (including mammalian, bird or fish) or plant proteins, synthetic polypeptides, haptens bound to macromolecular compounds, polysaccharides or antibodies.

The reagent capable of selectively binding the test analyte and calibrator analyte, respectively, (in the following termed "catching" reagent) may be an antibody reactive with the test or calibrator analyte, a cell surface receptor or a ligand-binding part thereof, a lectin, an antigen or an anti-idiotype antibody.

The antibody used as the catching reagent is preferably a monoclonal antibody or a fragment thereof such as a F(ab')$_2$ or Fab' fragment, e.g. prepared as described in A. Johnstone and R. Thorpe, *Immunochemistry in Practice*, 2nd Ed., Blackwell Scientific Publications, 1987, pp. 35–43. The antibody may also be a polyclonal antibody or a fragment thereof, e.g. prepared as described in A. Johnstone and R. Thorpe, op. cit., pp. 30–34 and 48–55.

The cell surface receptor used as the catching reagent in the method of the invention may be a glycoprotein or glycolipid receptor. Examples of suitable glycoprotein receptors (subject, of course, to the test analyte to be measured) are hormone or growth factor receptors, e.g. the insulin, insulin-like growth factor, epidermal growth factor, platelet-derived growth factor, transforming growth factor or colony stimulating factor receptors. A ligand-binding part of the receptor is suitably the extracellular domain of a glycoprotein receptor or a ligand-binding fragment thereof. The glycolipid receptor may be one which is capable of binding viral or bacterial surface peptides or proteins.

A lectin may be employed as the catching reagent in the method and test kit of the invention in cases where the test analyte comprises an appropriate carbohydrate moiety for which the lectin has affinity. Lectins are typically of plant origin and may, for instance, be lentil lectin, wheat germ lectin, peanut lectin, soybean lectin and concanavalin A.

When the test and calibrator analytes are both antibodies, the catching reagent may conveniently be a natural or synthetic antigen or an anti-idiotype antibody. The anti-idiotype antibody may be a monoclonal or polyclonal antibody or a fragment thereof, and may be prepared as indicated above.

The catching reagent may be immobilized directly on the solid support by physical adsorption or be bound covalently or through bridging molecules such as protein A, polylysine or an antibody (not reactive with the test or calibrator analyte, but reactive with the catching reagent) to the solid support. The solid support employed in the method and test kit of the invention preferably comprises a polymer. The polymer may be selected from the group consisting of a plastic (e.g. latex, a polystyrene, polyvinylchloride, polyurethane, polyacrylamide, polyvinylalcohol, nylon, polyvinylacetate, and any suitable copolymer thereof), cellulose (e.g. various types of paper, such as nitrocellulose paper and the like), a silicon polymer (e.g. siloxane), a polysaccharide (e.g. agarose or dextran), or an ion exchange resin (e.g. conventional anion or cation exchange resins).

The physical shape of the solid support is not critical, although some shapes may be more convenient than others for the present purpose. Thus, the solid support may be in the shape of a plate, e.g. a microtiter plate, or a paper strip, dipstick, membrane (e.g. a nylon membrane or a cellulose filter) or solid particles (e.g. latex beads).

In a favoured embodiment of the method and test kit of the invention, the solid support further comprises, in a third discrete area, a bound antibody which does not react with either the test or calibrator analyte. The purpose of including such a reagent is to control for background in the assay caused by heterophilic antibodies or non-specific binding, e.g. hydrophobic binding, of one or more sample components to the solid support.

Similarly to the catching reagent, the labelled reagent used in step (c) of the method of the invention may be an antibody reactive with the test or calibrator analyte, respectively, a cell surface receptor or a ligand-binding part thereof, a lectin, an antigen or an anti-idiotype antibody. Although it is possible to use different reagents in step (b) and (c) of the method of the invention, it is generally preferred to use the same reagent as the catching reagent and as the labelled reagent.

The label substance for the reagents used for binding to the test and calibrator analytes, respectively, is preferably selected from the group consisting of enzymes, coloured or fluorescent substances and radioactive isotopes.

Examples of enzymes useful as label substances are peroxidases (such as horseradish peroxidase), phosphatases (such as acid or alkaline phosphatase), β-galactosidase, urease, glucose oxidase, carbonic anhydrase, acetylcholinesterase, glucoamylase, lysozyme, malate dehydrogenase, glucose-6-phosphate dehydrogenase, β-glucosidase, proteases, pyruvate decarboxylase, esterases, luciferase, etc.

Enzymes are not in themselves detectable but must be combined with a substrate to catalyse a reaction the end product of which is detectable. Thus, a substrate may be added after step (c) of the present method resulting in the formation of a coloured or fluorescent substance. Examples of substrates which may be employed according to the invention include hydrogen peroxide/tetramethylbenzidine or chloronaphthole or o-phenylenediamine or 3-(p-hydroxyphenyl) propionic acid or luminol, indoxyl phosphate, p-nitrophenylphosphate, nitrophenyl galactopyranoside, 4-methyl umbelliferyl-D-galactopyranoside, or luciferin.

Alternatively, the label substance may comprise coloured or fluorescent substances, including gold particles, coloured or fluorescent latex particles, dye particles, fluorescein, phycoerythrin or phycocyanin.

Radioactive isotopes which may be used for the present purpose may be selected from I-125, I-131, H-3, P-35 and C-14.

In a particular embodiment of the test kit of the invention for use when two or more test analytes are to be quantitated simultaneously, the solid support is provided with a multiplicity of reagents for binding to different test analytes in discrete areas separate from each other as well as separate from the reagent for binding the calibrator analyte. This approach requires selection of a calibrator analyte exhibiting a standard curve which is comparable to those of the different test analytes to be determined. The test kit for use in this embodiment of the present method also comprises a multiplicity of labelled reagents, one for each test analyte.

DESCRIPTION OF PREFERRED EMBODIMENTS

In a currently preferred embodiment of the method of the present invention, (a) a known volume of sample suspected of containing the test analyte is mixed with a predetermined amount of bovine aprotinin as the calibrator analyte, (b) the mixture of step (a) is poured onto a membrane to which is bound, in a first discrete area, an antibody capable of selectively binding the test analyte and, in a second discrete area, an anti-aprotinin antibody, (c) a mixture of an enzyme-labelled antibody capable of selectively binding the test analyte and an enzyme-labelled anti-aprotinin antibody is poured onto the membrane in a manner ensuring an even distribution thereof over the membrane surface, and (d) determining the amount of test analyte in the sample by comparing the signal generated by enzyme-labelled antibody bound to the test analyte and to the aprotinin, respectively.

Hence, the preferred test kit to be employed in this embodiment is one wherein the calibrator analyte is aprotinin, the solid support is a membrane, the reagent capable of selectively binding the test analyte is an antibody reactive with the test analyte, the reagent capable of selectively binding the calibrator analyte is an anti-aprotinin antibody, and the label for each reagent is an enzyme.

In this embodiment of the present method, the mixture of the sample and aprotinin is preferably removed from the membrane subsequent to step (b). Furthermore, the mixture of enzyme-labelled antibodies is preferably removed from the membrane subsequent to step (c). Such removal may for instance be carried out by suction for which purpose the membrane may act as a filter. As such, it may suitably be a nylon-based membrane placed on a suction funnel.

The invention is further illustrated in the following examples which are not in any way intended to limit the scope of the invention as claimed.

EXAMPLE 1

Assay for CK-MB using myoglobin as the calibrator analyte A microporous membrane preactivated for covalently coup-ling of proteins (Pall Immunodyne immunoaffinity membrane) was placed in a Biodot microfiltration apparatus (available from BioRad) and coated with a monoclonal antibody reacting against human creatine kinase B subunit (available from Novo Nordisk A/S) in one well and with a monoclonal antibody reactive with human myoglobin (available from Novo Nordisk A/S) in another well. Coating buffer without antibody was added to a third well as a control. The membrane was then blocked with a 0.2% casein solution in phosphate buffered saline (PBS), pH 7.2.

Human myoglobin was added to a bovine serum sample containing human creative kinase M and B subunit (available from Novo Nordisk A/S) (CK-MB). 50 μl of this mixture was added to each well followed by 50 μl of a mixture of horseradish peroxidase (HRP)-conjugated monoclonal anti-human creatine kinase M subunit (available from Novo Nordisk A/S) and HRP-conjugated monoclonal anti-human myoglobin (available from Novo Nordisk A/S). These HRP- conjugated monoclonal antibodies were selected so as to be reactive with the analytes bound to the immobilized antibodies. One minute after addition of the conjugate mixture, the membrane was washed with 3×300 μl PBS, pH 7.2, containing 0.05% Tween 20 and 0.25M $(NH_4)_2SO_4$. 50 μl of a substrate solution containing hydrogen peroxide and tetramethylbenzidine was then added, and after 3 min the reaction was stopped by washing the membrane with distilled water containing 0.01% Naazide. A positive sample resulted in a blue spot. Finally, the response was read by means of a reflectometer (available from Shimadzu) and the measured reflectance was transformed according to the Kubelka-Munk equation to the entity K/S.

The myoglobin assay was adjusted through the concentration and composition of the reactants to give a calibration curve parallel to the CK-MB calibration curve. The myoglobin calibrator was then assigned CK-MB values by comparing the calibration curves for the two assays. An assigned CK-MB concentration value of the myoglobin calibrator means that quantitatively it elicits the same response in the myoglobin assay as the equivalent concentration of CK-MB in the creatine kinase assay.

The myoglobin calibrator used in the examples had an assigned CK-MB value of 25 ng/ml. Furthermore, the control was assigned a CK-MB concentration value of 0 ng/ml.

The CK-MB concentration in the sample was calculated by linear regression from the slope and intercept determined by the myoglobin analyte response and the background value.

The results shown in Table 1 and Table 2 below indicate that the myoglobin-calibrated CK-MB assay was able to quantitate the CK-MB concentration in a sample and that the values of the myoglobin-calibrated assay compared well to those obtained by conventional calibration using a set of CK-MB calibrators.

EXAMPLE 2

Assays were performed substantially as described in Example 1 with the exception that two parameters (sample volume and colour development time), which are known to exert a strong influence on this type of immunoassay, were varied. It appears from Tables 3 and 4 below that variations in these parameters result in considerable variations in the measured K/S values. However, the concentration of CK-MB determined was substantially unaffected by these variations.

TABLE 1

Quantitation of CK-MB conc.

| CK-MB conc* ng/ml | CK-MB system K/S | Background (0 ng CK-MB/ml)** K/S | Myoglobin system (25 ng CK-MB/ml)** K/S | CK-MB conc* ng/ml |
|---|---|---|---|---|
| 20 | 0.365 | 0.003 | 0.491 | 19 |
|  | 0.367 | 0.004 | 0.398 | 23 |
|  | 0.301 | 0.003 | 0.394 | 20 |
|  | 0.378 | 0.004 | 0.415 | 23 |
|  | 0.352 | 0.003 | 0.450 | 20 |
|  |  |  | Mean ± S.D. | 21 ± 2 |

*Bovine serum spiked with human CK-MB
**Assigned CK-MB value

TABLE 2

Comparison CK-MB concentration ng/ml

| True value* | Calibration with CK-MB system** | Calibration with myoglobin system*** |
|---|---|---|
| 20 | 19 | 21 |

*spiked with a known amount of CK-MB, the concentration verified by an assay commercially available for the quantitation of CK-MB (NovoClone EIA CK-MB)
**calculated using the assay described and CK-MB calib. 0, 10, 25, 50, and 100 ng/ml. Assay run in duplicate.
***From table 1

TABLE 3

Robustness. Variation in sample volume

| Sample volume μl | CK-MB system K/S | Background (0 ng CK-MB/ml)* K/S | Myoglobin system (25 ng CK-MB/ml)* K/S | CK-MB conc** ng/ml |
|---|---|---|---|---|
| 25 | 0.171 | 0.010 | 0.169 | 25 |
|  | 0.194 | 0.004 | 0.157 | 30 |
|  | 0.186 | 0.008 | 0.176 | 26 |
|  | 0.162 | 0.007 | 0.183 | 22 |
|  | 0.190 | 0.007 | 0.184 | 25 |
|  |  |  | Mean ± S.D. | 26 ± 3 |
| 50 | 0.412 | 0.007 | 0.389 | 27 |
|  | 0.378 | 0.015 | 0.350 | 27 |
|  | 0.410 | 0.010 | 0.367 | 28 |
|  | 0.455 | 0.010 | 0.420 | 27 |
|  | 0.435 | 0.008 | 0.458 | 24 |
|  |  |  | Mean ± S.D. | 27 ± 2 |
| 100 | 0.812 | 0.004 | 0.853 | 24 |
|  | 0.817 | 0.005 | 0.853 | 24 |
|  | 0.926 | 0.006 | 0.886 | 26 |
|  | 0.842 | 0.008 | 0.944 | 22 |
|  | 0.914 | 0.006 | 0.974 | 24 |
|  |  |  | Mean ± S.D. | 24 ± 1 |

*Assigned CK-MB value
**Calculated

TABLE 4

Robustness. Variation colour development time

| Colour development time minutes | CK-MB system K/S | Background (0 ng CK-MB/ml)* K/S | Myoglobin system (25 ng CK-MB/ml)* K/S | CK-MB conc* ng/ml |
|---|---|---|---|---|
| 1 | 0.158 | 0.011 | 0.227 | 18 |
|  | 0.143 | 0.008 | 0.121 | 29 |
|  | 0.132 | 0.011 | 0.124 | 25 |
|  | 0.121 | 0.012 | 0.141 | 21 |
|  | 0.123 | 0.009 | 0.166 | 19 |
|  |  |  | Mean ± S.D. | 22 ± 5 |
| 3 | 0 533 | 0.019 | 0.543 | 25 |
|  | 0.497 | 0.014 | 0.483 | 25 |

TABLE 4-continued

| Colour development time minutes | Robustness. Variation colour development time | | | |
|---|---|---|---|---|
| | CK-MB system K/S | Background (0 ng CK-MB/ml)* K/S | Myoglobin system (25 ng CK-MB/ml)* K/S | CK-MB conc* ng/ml |
| | 0.500 | 0.016 | 0.486 | 25 |
| | 0.569 | 0.019 | 0.474 | 30 |
| | 0.546 | 0.015 | 0.556 | 25 |
| | | | Mean ± S.D. | 26 ± 2 |
| 5 | 0.812 | 0.027 | 0.656 | 31 |
| | 0.848 | 0.029 | 0.797 | 26 |
| | 0.812 | 0.023 | 0.787 | 26 |
| | 0.817 | 0.020 | 0.880 | 23 |
| | 0.897 | 0.022 | 0.944 | 24 |
| | | | Mean ± S.D. | 26 ± 3 |

*Assigned CK-MB value
**Calculated

What is claimed is:

1. An assay for determining the amount of a test analyte contained in a sample, comprising the following sequential steps:
   (a) providing a mixture of a known volume of said sample and a known amount of a calibrator analyte, wherein said calibrator analyte is foreign to said sample and the behavior of said calibrator analyte is comparable to that of said test analyte under the same assay conditions;
   (b) contacting said mixture with a solid support, wherein said solid support comprises a first reagent capable of selectively binding said test analyte bound to a first discrete area of said solid support and a second reagent capable of selectively binding said calibrator analyte bound to a second discrete area of said solid support;
   (c) contacting said solid support with a first labelled substance capable of selectively binding said test analyte and a second labelled substance capable of selectively binding said calibrator analyte, wherein said first and second labelled substances use an identical label; and
   (d) determining the amount of said test analyte in said sample by comparing the level of said first labelled substance bound to said test analyte and of said second labelled substance bound to said calibrator analyte.

2. The assay according to claim 1, wherein said calibrator analyte is an animal or a plant protein which does not cross-react with said test analyte.

3. The assay according to claim 2, wherein said calibrator analyte is selected from the group consisting of aprotinin, a synthetic polypeptide, a hapten bound to a macromolecular compound, a polysaccharide, and an antibody.

4. The assay according to claim 2, wherein said test analyte is selected from the group consisting of a hormone, a blood component, a coagulation factor, a protease, a growth factor, a microbial component, a pancreatic amylase, a heart structural protein, a C-reactive protein, a α-foetoprotein, a creatine kinase type MB, a creatine kinase type MM, a bacterial or a viral surface protein, and an antibody.

5. The assay according to claim 4, wherein said test analyte is a hormone selected from the group consisting of insulin, a growth hormone, a chorionic gonadotropin, a luteinizing hormone, a follicle stimulating hormone, and a steroid hormone.

6. The assay according to claim 4, wherein said test analyte is a blood component selected from the group consisting of a blood coagulation factor, a protease, and a precursor of a protease.

7. The assay according to claim 4, wherein said test analyte is a coagulation factor selected from the group consisting of Factor VII, Factor VIII, Factor IX, Factor X, and Factor XIII.

8. The assay according to claim 4, wherein the test analyte is a protease selected from the group consisting thrombin, prothrombin, plasmin, plasminogen, and tissue plasminogen activator.

9. The assay according to claim 4, wherein said test analyte is a growth factor selected from the group consisting of insulin-like growth factor, platelet-derived growth factor, epidermal growth factor, colony stimulating factor, transforming growth factor, and fibroblast growth factor.

10. The assay according to claim 4, wherein said test analyte is a microbial component selected from the group consisting of cholera toxin, diphtheria toxin, Salmonella toxin, Shiga toxin, Clostridium botulinum toxin, aflatoxin, endotoxin, and Chlamydia-specific antigen.

11. The assay according to claim 1, wherein said test analyte is selected from the group consisting of a creatine kinase type MB, a creatine kinase type MM, a pancreatic amylase, a heart structural protein, a C-reactive protein, a α-foetoprotein, and a Chlamydia-specific antigen.

12. The assay according to claim 1, wherein said sample is selected from the group consisting of a body fluid, a tissue extract, a culture medium in which a cell has been grown, and a foodstuff.

13. The assay according to claim 12, wherein the body fluid is one selected from the group consisting of blood, serum, plasma, amniotic fluid, sputum, urine, cerebrospinal fluid, lymph, tear fluid, feces, and gastric fluid.

14. The assay according to claim 1, wherein said first reagent is selected from the group consisting of an antibody reactive with said test analyte, a cell surface receptor, a ligand-binding part of a cell surface receptor, a lectin, an antigen, and an anti-idiotype antibody.

15. The assay according to claim 14, wherein said first reagent is a monoclonal antibody or a polyclonal antibody.

16. The assay according to claim 14, wherein said first reagent is a glycoprotein or a glycolipid receptor.

17. The assay according to claim 14, wherein said first reagent is selected from the group consisting of lentil lectin, wheat germ, lectin, peanut lectin, soybean lectin and concanavalin A.

18. The assay according to claim 14, wherein said first reagent is a natural or synthetic antigen containing at least one epitope which is reactive with a test analyte antibody.

19. The assay according to claim 14, wherein said first reagent is an anti-idiotype antibody which is reactive with a test analyte antibody.

20. The assay according to claim 14, wherein said first reagent is a monoclonal or a polyclonal antibody.

21. The assay according to claim 1, wherein said second reagent is selected from the group consisting of an antibody reactive with the calibrator analyte, a cell surface receptor, a ligand-binding part a cell surface receptor, an antigen, a lectin, and an anti-idiotype antibody.

22. The assay according to claim 21, wherein said second reagent is a monoclonal or polyclonal antibody.

23. The assay according to claim 21, wherein said second reagent is a glycoprotein or a glycolipid receptor.

24. The assay according to claim 21, wherein said second reagent is a lectin selected from the group consisting of lentil lectin, wheat germ lectin, peanut lectin, soybean lectin, and concanavalin A.

25. The assay according to claim 21, wherein said second reagent is an anti-idiotype antibody which is reactive with a calibrator analyte antibody.

26. The assay according to claim 25, wherein said second reagent is a monoclonal or a polyclonal antibody.

27. The assay according to claim 1, wherein the label of said first and second labelled substances is selected from the group consisting of an enzyme, a colored substance, a fluorescent substance, and a radioactive isotope.

28. The assay according to claim 1, wherein said calibrator analyte is aprotinin and said second reagent is an anti-aprotinin antibody.

29. The assay according to claim 28, wherein said first labelled substance is an enzyme-labelled antibody, and said second labelled substance is an enzyme labelled anti-aprotinin antibody.

30. The assay according to claim 28, wherein said test analyte is selected from the group consisting of a creatine kinase type MB, a creatine kinase type MM, a pancreatic amylase, a heart structural protein, a C-reactive protein, a α-foetoprotein, and a Chlamydia-specific antigen.

31. The assay according to claim 1, wherein said solid support further comprises an antibody nonreactive with either the test or calibrator analyte bound to a third discrete area of said solid support.

32. The assay according to claim 1, wherein said solid support further comprises one or more additional reagents capable of selectively binding to one or more additional test analytes bound to discrete areas of said solid support, and step (c) further comprises contacting said solid support with one or more additional labelled substances each capable of selectively binding said one or more additional test analytes, wherein said one or more additional labelled substances use the identical label.

33. A test kit for determining the amount of a test analyte in a sample, comprising
(a) a first container comprising a known amount of a calibrator analyte, wherein said calibrator analyte is foreign to said sample and the behavior of said calibrator analyte is comparable to that of said test analyte under the same assay conditions;
(b) a solid support comprising a first reagent capable of selectively binding said test analyte bound to a first discrete area of said solid support and a second reagent capable of selectively binding said calibrator analyte bound to a second discrete area of said solid support;
(c) a second container comprising a first labelled substance capable of selectively binding the test analyte; and
(d) a third container comprising a second labelled substance capable of selectively binding the calibrator analyte; wherein said first and second labelled substances use an identical label.

34. The test kit according to claim 33, wherein the second and third containers are the same container.

35. The test kit according to claim 33, wherein said calibrator analyte is an animal or a plant protein which does not cross-react with the test analyte.

36. The test kit according to claim 35, wherein said calibrator analyte is selected from the group consisting of an aprotinin, a synthetic polypeptide, a hapten bound to a macromolecular compound, a polysaccharide, and an antibody.

37. The test kit according to claim 33, wherein said first reagent is selected from the group consisting of an antibody reactive with said test analyte, a cell surface receptor, a ligand-binding part of a cell surface receptor, a lectin, an antigen, and an anti-idiotype antibody.

38. The test kit according to claim 37, wherein said first reagent is a monoclonal or a polyclonal antibody or a fragment thereof.

39. The test kit according to claim 37, wherein said first reagent is a glycoprotein or a glycolipid receptor.

40. The test kit according to claim 37, wherein said first reagent is selected from the group consisting of lentil lectin, wheat germ lectin, peanut lectin, soybean lectin, and concanavalin A.

41. The test kit according to claim 37, wherein said first reagent is a natural or synthetic antigen containing at least one epitope which is reactive with a test analyte antibody.

42. The test kit according to claim 37, wherein said first reagent is an anti-idiotype antibody which is reactive with a test analyte antibody.

43. The test kit according to claim 33, wherein said second reagent is selected from the group consisting of an antibody reactive with said calibrator analyte, a cell surface receptor, a ligand-binding part of a cell surface receptor, an antigen, a lectin, and an anti-antibody.

44. The test kit according to claim 43, wherein said second reagent is a monoclonal or polyclonal antibody.

45. The test kit according to claim 43, wherein said second reagent is a glycoprotein or a glycolipid receptor.

46. The test kit according to claim 43, wherein said second reagent is selected from the group consisting of lentil lectin, wheat germ lectin, peanut lectin, soybean lectin, concanavalin A.

47. The test kit according to claim 43, wherein said second reagent is an anti-idiotype antibody which is reactive with a calibrator analyte antibody.

48. The test kit according to claim 47, wherein said second reagent is a monoclonal or polyclonal antibody or a fragment thereof.

49. The test kit according to claim 33, wherein said solid support is a polymer or a ceramic material.

50. The test kit according to claim 49, wherein said polymer is selected from the group consisting of plastic, a polysaccharide, an ion exchange resin, a cellulose polymer, and a silicon polymer.

51. The test kit according to claim 49, wherein said ceramic material is glass.

52. The test kit according to claim 49, wherein said solid support is selected from the group consisting of a plate, a paper strip, a dipstick, a membrane, and a solid particle.

53. The test kit according to claim 33, wherein said solid support further comprises an antibody nonreactive with either the test or calibrator analyte bound to a third discrete area of said solid support.

54. The test kit according to claim 33, wherein the label of said first and second labelled substances is selected from the group consisting of an enzyme, a colored substance, a fluorescent substance, and a radioactive isotope.

55. The test kit according to claim 33, further comprising one or more additional containers comprising one or more additional reagents capable of selectively binding to one or more additional test analytes bound to discrete areas of said solid support, and one or more additional containers comprising one or more additional labelled substances each capable of selectively binding said one or more additional test analytes, wherein said one or more additional labelled substances use the identical label.

* * * * *